(12) United States Patent
Misselbrook et al.

(10) Patent No.: US 6,387,388 B1
(45) Date of Patent: May 14, 2002

(54) PESTICIDAL FORMULATION

(75) Inventors: John Misselbrook, Southampton (GB); Robert F. Peterson, Jr., Abington, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/318,111

(22) Filed: May 25, 1999

(Under 37 CFR 1.47)

Related U.S. Application Data

(63) Continuation of application No. 09/146,463, filed on Sep. 3, 1998, now abandoned, which is a continuation of application No. 08/744,809, filed on Nov. 6, 1996, now abandoned

(60) Provisional application No. 60/006,346, filed on Nov. 8, 1995.

(51) Int. Cl.$^7$ .............................................. A01N 25/12
(52) U.S. Cl. ...................... 424/409; 424/405; 424/406; 424/417; 514/30
(58) Field of Search ........................ 424/405, 408–409, 424/717–421; 514/30, 29, 28

(56) References Cited

U.S. PATENT DOCUMENTS

| | | | |
|---|---|---|---|
| 3,090,723 A | | 5/1963 | Pastac |
| 4,411,694 A | | 10/1983 | Smith et al. |
| 4,439,488 A | * | 3/1984 | Trimnell et al. ........ 428/402.24 |
| 4,834,977 A | | 5/1989 | Kohama et al. |
| 5,288,710 A | | 2/1994 | Cvetovich |
| 5,656,615 A | * | 8/1997 | Camden ...................... 514/76 |
| 5,714,157 A | | 2/1998 | Sandell et al. |

FOREIGN PATENT DOCUMENTS

| | | |
|---|---|---|
| DE | 4 336 307 | 4/1995 |
| EP | 0 112 438 | 4/1984 |
| GB | 2221621 | * 2/1990 |
| GB | 2 238 960 | 6/1991 |
| JP | 5 6081 510 | 7/1981 |
| JP | 6 092 803 | 4/1994 |
| WO | WO 90/12503 | 11/1990 |
| WO | WO 95/00153 | 1/1995 |
| WO | WO 95/20877 | 8/1995 |

OTHER PUBLICATIONS

Banaker, "Role of Ingredients and Exceipients in Developing Pharmaceuticals", *Manufacturing Chemist*, p. 32 (Apr. 1994).

J.L. Hudson and O.R. Tarwater, "Reduction of Pesticide Toxicity by Choices of Formulation" *ACS Symposium series#371. Pesticide Formulations*, Ch. 11, pp. 124–130 (1988).

Lerk, C.F., "Consolidation and Compaction of Lactose", *Drug Development and Industrial Pharmacy*, 19, 2359 (1993).

Derwent WPI Database, Abstract 94–147816, "Water Soluble agricultural chemical granules—comprise water soluble agricultural chemical active component", *Japan Patent Pub.* JP 6092 803 (Apr. 5, 1994).

Food and Agriculture Organization of the United Nations, "Manual of the Development and Use of FAO Specification for Plant Protection Products", *FAO Plant Production and Protection Paper#85*, Appendix C, pp. 96–104 1985.

\* cited by examiner

*Primary Examiner*—Neil S. Levy
(74) *Attorney, Agent, or Firm*—J. Eric Thies; David L. Rose

(57) ABSTRACT

The present invention is directed to a pesticidal composition of a water-soluble pesticide and processes for its manufacture. More specifically, the invention relates to a soluble granule (SG) pesticidal formulation comprising a water-soluble pesticide and a water-soluble filler. The present invention provides a pesticidal formulation with efficacy equal to the corresponding liquid formulation, yet with improved handler safety, such as lower eye irritation.

11 Claims, No Drawings

PESTICIDAL FORMULATION

CROSS REFERENCE TO RELATED APPLICATIONS

This application is a continuation of U.S. Ser. No. 09/146,463, filed Sep. 3, 1998, ABD, which is a continuation of U.S. Ser. No. 08/744,809, filed Nov. 6, 1996, ABD, which claims priority under 35 U.S.C. § 119(e) from U.S. Ser. No. 60/006,346, filed Nov. 8, 1995.

FIELD OF THE INVENTION

The present invention relates to pesticidal compositions comprising a water-soluble pesticide and process for their manufacture. More specifically, the invention relates to soluble granule (SG) formulations comprising a water-soluble pesticide and a water-soluble filler.

BACKGROUND OF THE INVENTION

Emulsifiable concentrate (EC) agricultural formulations of pesticides are well known in the art. These formulations generally comprise emulsifying and dispersing agents in addition to the pesticide to give a uniform solution. However, these agricultural formulations suffer numerous drawbacks because they are liquid. In particular, liquid pesticidal formulations must be handled carefully to minimize safety concerns, particularly dermal and ocular irritation.

Although solvent-free pesticidal compositions are known, most solvent-free pesticidal formulations have lower bioactivity than the corresponding emulsifiable concentrate formulations. Thus, one skilled in the art frequently has been forced to choose between using a solvent to give a more bioactive formulation but with higher dermal and ocular toxicity, or having a less active solid formulation.

The present invention overcomes the drawbacks of liquid formulations by taking advantage where possible of the water solubility of the pesticide to furnish a composition in divided form so that it will dissolve in water.

Certain methods for preparing water-soluble granules of pesticides are known in the art. PCT Publication No. WO 90/12503 discloses the formation of alkaline salts of soluble acidic or phenolic pesticides to give a granular composition. U.S. Pat. No. 4,511,395 discloses wettable herbicidal powder compositions which comprise a swelling hydrous silicate clay. EPO Publication No. EP 0,111,112 discloses pesticide granules comprising an inert carrier and a pesticide, and which are coated with finely divided silica.

The use of lactose as a solid filler to make tablets is well known in the pharmaceutical industry. (See e.g. Lerk, C. F., "Consolidation and Compaction of Lactose" *Drug Development and Industrial Pharmacy*, 19, 2359 (1993); "Role of Ingredients and Excipients in Developing Pharmaceuticals" *Manufacturing Chemist*, p. 32 (April 1994). Nevertheless, the use of lactose or other water-soluble fillers as agricultural inert ingredients is not common in formulating pesticides for crop protection. Hudson and Tarwater (Reduction of Pesticide Toxicity by Choices of Formulation, J. L. Hudson and O. R. Tarwater, in *ACS Symposium series* #371, *Pesticide Formulations*, B. Cross and H. B. Scher, eds.) discuss the effect the choice of formulation on toxicity, and state (on p. 129) that the ocular irritation can be very different for different formulations of the same active ingredient, and that changes in the other toxicity categories may occur. Nevertheless, they do not discuss how such diminished toxicity may be achieved. Furthermore, they mention wettable powders (WP), water dispersible granules (WDG) or dry flowables (DF), but they do not even mention soluble granule (SG) formulations.

The soluble granule (SG) formulation of the present invention has numerous advantages over the corresponding liquid formulation of a given pesticide. Because it is a solid, the SG formulation exhibits improved ease of handling relative to the liquid formulation. Nevertheless, when dissolved in water the SG formulation provides a clear solution which is aesthetically pleasing. The SG formulation also minimizes the use of ingredients of environmental concern by eliminating the need for volatile organic compounds and employing fillers which are biologically derived, thereby diminishing the potential environmental impact. In addition, formulations of higher concentration (hence lower cost per kg of active ingredient formulated) can be achieved without any loss in biological activity with respect to a liquid formulation. Because the dried granules in the SG formulation are of roughly constant bulk density, the granules may be measured by volume, thus making them equally convenient to liquid formulations in ease of use.

More importantly, however, use of the instant SG formulation is less risky to personnel than the corresponding liquid formulation. Risk of exposure is generally evaluated under the guide: risk=hazard×exposure. Because the instant SG formulation is less toxic, the hazard is decreased. In addition, the probability of contact is lower when the material is in a solid rather than a liquid form and hence the degree of exposure is also reduced. The present invention also affords relatively hard non-dusty granules, thereby even further diminishing the risk of exposure to dust from the composition. Also, the present invention may be practiced without the use of mineral fillers which contain crystalline silica, a known carcinogen. Thus, the present invention diminishes the risk of exposure and provides greater handler safety, especially with regard to ocular irritation, than a liquid formulation.

Accordingly, the present invention provides a relatively safe, bionatural delivery system for a pesticide which is water soluble at the concentration at which it is employed.

SUMMARY OF THE INVENTION

The present invention relates to a pesticidal composition of a water-soluble pesticide and processes for its manufacture. More specifically, the invention relates to a soluble granule (SG) pesticidal formulation comprising a water-soluble pesticide and a water-soluble filler. The present invention provides a pesticidal formulation with efficacy equal to the corresponding liquid formulation, yet with improved handler safety, such as lower eye irritation.

DETAILED DESCRIPTION OF THE INVENTION

The present invention is directed to an pesticidal composition comprising a water-soluble pesticide and processes for its manufacture. More specifically, the invention relates to a soluble granule (SG) formulation comprising a water-soluble pesticide, such as emamectin benzoate, and a water-soluble filler, such as lactose.

The pesticidal composition of the present invention comprises: a water-soluble pesticide; and a water-soluble filler.

The present pesticidal composition may further comprise: a wetting surfactant; and/or a dispersing surfactant. Optionally, a defoaming agent may also be present.

Preferably the water-soluble pesticide is selected from: emamectin or an agriculturally acceptable salt thereof. Preferably the water-soluble filler is selected from: lactose, sucrose, glucose, and the like. Preferably the wetting surfactant is selected from: sodium N-methyl-N-oleyl taurate, sodium N-methyl-N-palmityl taurate, sodium N-methyl-N-oleoyl taurate, sodium dioctyl sulfosuccinate and other sodium alkyl sulfosuccinates, sodium lauryl sulfate, alpha-(p-nonylphenyl)-omega-hydroxy poly(oxyethylene) with an average of 8–12 moles of ethylene oxide, and alpha-(p-octylphenyl)-omega-hydroxy poly(oxyethylene) with an average of 7–12 moles of ethylene oxide. Preferably the dispersing surfactant is selected from: sodium alkyl naphthalene sulfonate, sodium napthalene sulfonate, calcium lignosulfonate, sodium lignosulfonate, and ammonium lignosulfonate. Preferably the defoaming agent is selected from: methylated silicones, polyorganosiloxane, and 2-ethylhexanol.

More preferably the water-soluble pesticide is emamectin or emamectin benzoate. More preferably the water-soluble filler is lactose. More preferably the wetting surfactant is sodium N-methyl N-oleyl taurate. More preferably the dispersing surfactant is sodium alkyl naphthalene sulfonate. More preferably the defoaming agent is polyorganosiloxane.

The pesticidal composition of the present invention may be provided in the form of a wettable powder but preferably is in the form of a water-soluble granule. Similarly, the pesticidal composition of the present invention may be provided as an aggregate, a matrix, or a monolith, such as a brick, pellet, tablet, stick, film, sheet, and the like. Preferably, the pesticidal composition of the present invention is embedded in a water-soluble matrix or monolith. It also will be appreciated by one skilled in the art that the present invention further includes encasement of the instant pesticidal compositions in a water-soluble package, such as a pouch, sachet, bag, capsule, and the like.

The pesticidal compositions of the present invention comprise 0.1 to 90% by weight of a water-soluble pesticide, preferably emamectin benzoate; and 30 to 99.9% by weight of a water-soluble filler, preferably lactose (not to the exclusion of other ingredients).

It will be appreciated by one skilled in the art that the sum of the proportions of the water-soluble pesticide and the water-soluble filler are not greater than 100% by weight and that the exact concentrations of the components may vary depending on the presence of impurities.

In a more preferred embodiment, the pesticidal compositions of the present invention comprise 0.1 to 60% by weight of a water-soluble pesticide, preferably emamectin benzoate; 40 to 99.9% by weight of a water-soluble filler; 0 to 50% by weight of a wetting surfactant; 0 to 50% by weight of a dispersing surfactant; 0 to 5% by weight of a defoaming agent (not to the exclusion of other ingredients).

It will be appreciated by one skilled in the art that the sum of the proportions of the water-soluble pesticide, the water-soluble filler, the wetting surfactant, the dispersing surfactant and the defoaming agent are not greater than 100% by weight and the exact concentrations of the components may vary depending on the presence of impurities.

In one embodiment of the present invention the formulation contains about 0.1 to 90% by weight of the water-soluble pesticide.

Preferred pesticidal compositions of the present invention comprise 0.1 to 60% by weight of emamectin benzoate; 40 to 99.9% by weight of lactose; 0 to 25% by weight of sodium N-methyl N-oleyl taurate; 0 to 10% by weight of sodium alkyl naphthalene sulfonate; and 0 to 3% by weight of polyorganosiloxane (not to the exclusion of other ingredients).

More preferred pesticidal compositions of the present invention comprise 1 to 50% by weight of emamectin benzoate; 40 to 99% by weight of lactose; 0 to 10% by weight of sodium N-methyl N-oleyl taurate; 0 to 2% by weight of sodium alkyl naphthalene sulfonate; and 0 to 1% by weight of polyorganosiloxane (not to the exclusion of other ingredients). Even more preferred pesticidal compositions are those which may comprise 1 to 20% by weight of emamectin benzoate.

Even more preferred pesticidal compositions of the present invention comprise 1 to 20% by weight of emamectin benzoate; 60 to 99% by weight of lactose; 5 to 10% by weight of sodium N-methyl N-oleyl taurate; 0.5 to 2% by weight of sodium alkyl naphthalene sulfonate; and 0 to 0.5% by weight of polyorganosiloxane (not to the exclusion of other ingredients). Still more preferred pesticidal compositions are those which comprise 1 to 10% by weight of emamectin benzoate.

It will be appreciated by one skilled in the art that the sum of the proportions of emamectin benzoate, lactose, sodium N-methyl N-oleyl taurate, sodium alkyl naphthalene sulfonate and polyorganosiloxane are not greater than 100% by weight and that the exact concentrations of the components may vary depending on the presence of impurities.

Especially preferred pesticidal formulations are as follows:

Soluble granules comprising about 5.3% by weight of emamectin benzoate; about 86% by weight of lactose; about 7.5% by weight of sodium N-methyl N-oleyl taurate; about 1% by weight of sodium alkyl naphthalene sulfonate; about 0.1% by weight of polyorganosiloxane.

The present invention further includes a process for preparing a soluble granule formulation which process comprises:

(1) forming a powder blend of a water-soluble pesticide and a water-soluble filler;

(2) adding water to the blend;

(3) extruding the wet blend through a die to form granules; and (4) drying the granules to remove the water.

The present invention is further directed to a soluble granule formulation prepared by such process.

In a preferred embodiment, the process for preparing a soluble granule formulation comprises:

(1) forming a powder blend of a water-soluble pesticide, a water-soluble filler, a wetting surfactant and a dispersing surfactant;

(2) adding water to the blend;

(3) extruding the wet blend through a die to form granules; and (4) drying the granules to remove the water.

Optionally, in this process a defoaming agent may be added to the powder blend.

The present invention is further directed to a soluble granule formulation prepared by such process.

Specifically exemplifying the present invention is the process comprising the steps of:

(1) forming a powder blend of a emamectin benzoate and lactose;

(2) adding water to the blend;

(3) extruding the wet blend through a die to form granules; and (4) drying the granules to remove the water.

A preferred embodiment which specifically exemplifies the present invention is the process comprising the steps of:

(1) forming a powder blend of a emamectin benzoate, lactose, sodium alkyl naphthalene sulfonate, sodium N-methyl N-oleyl taurate, and polyorganosiloxane;
(2) adding water to the blend;
(3) extruding the wet blend through a die to form granules; and
(4) drying the granules to remove the water.

The present invention is further directed to a soluble granule formulation of emamectin benzoate prepared by such process.

The present invention is further directed to a delivery system for water-soluble pesticides, in particular, emamectin benzoate, which comprises soluble granules and the use thereof.

The present invention further provides a method for administering the water-soluble pesticide comprising:
(1) formulating the water-soluble pesticide as a soluble granule;
(2) mixing with water a portion of the soluble granule sufficient to give the desired amount of active ingredient of the water-soluble pesticide; and
(3) applying the pesticide/water mixture.

The present invention is further directed to a pesticide/water mixture prepared by such process.

The application of the pesticide/water mixture may be conducted by methods well known in the art, including, spraying, misting, dripping, infusing, injecting, irrigating, and the like.

The term "water-soluble pesticide" as used herein includes any biologically active pesticidal agent or crop protection chemical which is water soluble at the concentration in which it is employed (i.e. the agent is water soluble at the volume used in field application). Such water-soluble pesticides include certain fungicides, herbicides, such as plant growth regulators, and insecticides, such as nematocides, anti-helmentics, and miticides. Exemplary water-soluble pesticides which may be employed in the present invention include: the fungicides: blasticidin-S, kasugamycin, and hymexanol; the herbicides: acifluorfen, glyphosate, and glufosinate; the plant growth regulants: gibberellic acid, maleic hydrazide and dikegulac; and the insecticides: acephate, emamectin, and emamectin benzoate. A particularly preferred water-soluble pesticide is emamectin, or an agriculturally acceptable salt thereof, such as the salt formed with benzoic acid, salicyclic acid, gallic acid, benzenesulfonic acid, hydrochloric and citric acid, especially emamectin benzoate. One skilled in the art will readily appreciate that these pesticides exhibit sufficient water solubility that they will dissolve when mixed with water at the labeled use rate. For example, commercial label use rates of acephate are as high as 1.33 lb (0.60 kg) in a minimum of 3 gallons (11.4 liters) of water. Because 650 g of acephate is soluble in 1 liter of water, the acephate is fully soluble in water at its maximum label use rate. Similarly, emamectin benzoate is soluble at about 100 ppm in water. Thus, at a typical use rate 3.4 g of emamectin benzoate will be soluble in about 34 liters of water.

The term "water-soluble granule" as used herein is intended to include any granular or pelletized compositions which permit the active ingredient to be in solution after dissolving in water. It is not necessary for all of the ingredients of the water-soluble granule to be in solution as long as the active ingredient itself is in solution. Thus, the present invention includes within its scope water-soluble granules in which some of the ingredients may be relatively insoluble. The actual physical form of the instant pesticidal composition is not critical to the proper function of the present invention.

The term "water-soluble filler" as used herein includes any water soluble or water dispersible agent which may be employed to dilute the pesticide. Preferred water-soluble agents include those which are biologically derived. Appropriate water-soluble fillers include lactose, glucose, fructose, mannose, mannitol, sucrose, such as confectioner's sugar, black sugar, brown sugar, soft brown sugar, other sugars or saccharides, microcrystalline cellulose, powdered cellulose, calcium phosphate(s), inorganic water-soluble salts, and the like, and mixtures thereof. Examples of lactose which can be used in the present invention include hydrated $\alpha$-lactose, anhydrous $\alpha$-lactose, hydrated $\beta$-lactose, anhydrous $\beta$-lactose, and the like, and mixtures thereof.

Any surfactants can be used as the surfactant in the present invention, as long as it will emulsify the desired pesticide, or the pesticide when mixed with water. Examples of such surfactants include glycerine fatty acid esters, sucrose fatty acid esters, sorbitan fatty acid esters, fatty acid salts, alkyl sulfates, alkylbenzene sulfonic acid salts, alkyl aryl ethers and polyoxyethylenated products thereof, ethylene oxide addition products of higher alcohols, polyoxyethylene polyoxypropylene glycol, lignin sulfonic acid salt, polyoxyethylene styrylphenyl ether, polyoxyethylene alkyl esters, alkyl aryl sulfates, and the like. The surfactants may be used singly or in a suitable combination. Surfactants which can uniformly mix with the desired pesticide or the pesticides and water are preferred but it is not always necessary to use such surfactants. It is sufficient that surfactants be dissolved in water when the pesticidal composition is diluted with water.

The term "wetting surfactant" as used herein includes any agent which may be employed to enhance the wetting properties of the formulation such as sodium N-methyl-N-oleyl taurate, sodium N-methyl-N-palmityl taurate, sodium N-methyl-N-oleoyl taurate, sodium dioctyl sulfosuccinate and other sodium alkyl sulfosuccinates, sodium lauryl sulfate, alpha-(p-nonylphenyl)-omega-hydroxy poly(oxyethylene) with an average of 8–12 moles of ethylene oxide, and alpha-(p-octylphenyl)-omega-hydroxy poly(oxyethylene) with an average of 7–12 moles of ethylene oxide.

The term "dispersing surfactant" as used herein includes any agent which may be employed to enhance the dispersion of the formulation when mixed in water such as sodium alkyl naphthalene sulfonate, sodium naphthalene sulfonate, calcium lignosulfonate, sodium lignosulfonate, and ammonium lignosulfonate.

The term "defoaming agent" as used herein includes any agent which may be employed to reduce the tendency of the formulation to induce the generation of foam when added to water such as methylated silicones, polyorganosiloxane, and 2-ethylhexanol.

In addition to the pesticide, the water-soluble filler, the wetting surfactant, the dispersing surfactant and the defoaming agent, the instant pesticidal compositions may also appropriately contain stabilizers, synergists, coloring agents, etc.

The pesticidal compositions of the present invention are generally spread after diluting with water. One skilled in the art will appreciate that when diluted with water, the dilution magnification of the pesticidal composition varies depending upon the kind of pesticide, the kind of harmful organism to be controlled, the kind of crops to be treated, the kind of blight to be mitigated, the kind of weeds to be controlled, the time period for treatment, the method of application, etc. and is not definitively given but is generally in a range of from 20 to 10,000 times.

A preferred water-soluble pesticide for use in the formulations of the present invention is emamectin benzoate. Certain avermectin B1a/B1b compounds which have activity as agricultural insecticides are disclosed in U.S. Pat. No. 4,310,519 (issued Jan. 12, 1982). The compound 4"deoxy4"-epi-methylamino avermectin hydrochloride is disclosed in U.S. Pat. No. 4,874,749 (issued Oct. 17, 1989) as having properties as an agricultural insecticide. Stable salts of 4"-deoxy-4"-epi-methylamino avermectin B1a/B1b are disclosed in U.S. Pat. No. 5,288,710 (issued Feb. 22, 1994).

In particular, U.S. Pat. No. 5,288,710 discloses the benzoate salt of 4"-deoxy-4"-epi-methylamino avermectin B1a/B1b (emamectin benzoate) which has the structure, e.g.:

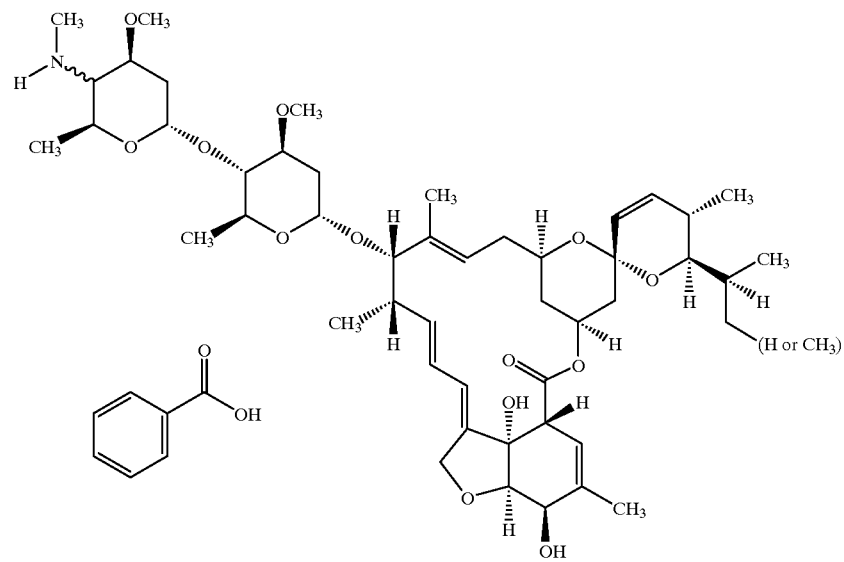

This compound may be readily prepared by the methodology describe therein. The other ingredients in the subject formulations are either commercially available, or are readily prepared by methods known in the art.

The use of the present formulations will be readily apparent to one skilled in the art. In particular, formulations comprising emamectin benzoate may be utilized e.g. as described in U.S. Pat. No. 5,288,710.

The pesticidal compositions of the present invention may be used to exterminate or control harmful organisms or regulate plant growth.

The pesticidal compositions of the present invention are particularly useful in combating agricultural pests that inflict damage upon crops while they are growing or while in storage. The compounds are applied using known techniques as sprays, dusts, emulsions and the like, to the growing or stored crops to effect protection from such agricultural pests.

For example, the compound emamectin and the agriculturally acceptable salts thereof, in particular, emamectin benzoate exhibit significant parasiticidal activity as anthelmintics, ectoparasiticides, insecticides and acaricides, in human and animal health and in agriculture.

Emamectin and the agriculturally acceptable salts thereof are useful against insect pests of stored grains such as Tribolium sp., Tenebrio sp., and of agricultural plants such as spider mites, (Tetranychus sp.), aphids, (Acyrthiosiphon sp.); against migratory orthopterans such as locusts and immature stages of insects living on plant tissue. These pesticides are useful as a nematocide for the control of soil nematodes and plant parasites such as Meloidogyne sp. which may be of importance in agriculture. These pesticides are also active against other plant pests such as the southern army worm and Mexican bean beetle larvae. These pesticides also have activity against Dirofilaria in dogs; Namatospiroides, Syphacia, Aspiculuris in rodents; the arthropod ectoparasites of animals and birds such as ticks, mites, lice, fleas, and blowfly; in sheep Lucilia sp.; biting insects and such migrating diperous larvae as Hypoderma sp. in cattle; Gastrophilus in horses; and Caterebra sp. in rodents. In addition these compounds are also active against parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridis, Oxyuris, Ancylostoma, Uncinaria, Toxascaris and Parascaris. Certain of these, such as Nematodirus, Cooperia and Oesphagostomum attack primarily the intestinal tract while others, such as Haemonchus and Ostertagia, are more prevalent in the stomach while still others such as Dictyocaulus are found in the lungs. These pesticides are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and, other dipterous pests causing annoyance to man. These pesticides are also active against household pests such as the cockroach, Blatella sp., clothes moth, Tineola sp., Carpet beetle, Attagenus sp., and the housefly *Musca domestica*.

If desired, the pesticidal compositions of the present invention may be employed to formulate a liquid drench. The drench is normally a solution, suspension or dispersion of the active ingredient usually in water together with suspending agent such as bentonite and a wetting agent or like excipient. Generally, the drenches also contain an antifoaming agent.

The optimum amount of pesticide to be employed for best results will, of course, depend upon the particular pesticide employed, the species of animal or plant to be treated and the type and severity of parasitic infection or infestation. The optimum amount of pesticide to be employed is considered to be readily determined by one skilled in the art without undue experimentation.

Methods for preparing the formulations of the present invention are illustrated in the following Examples. The following examples are given for the purpose of illustrating the present invention and shall not be construed as being limitations on the scope or spirit of the instant invention.

EXAMPLE 1

Representative compositions of the emulsifiable concentrate (EC) formulation and of the soluble granule (SG) formulation are given below:

Emulsifiable Concentrate Formulation of Emamectin Benzoate

| Ingredient | Trade name | % w/w |
| --- | --- | --- |
| Emamectin Benzoate | (Technical AI) | 2.40 |
| Butylated hydroxytoluene | BHT | 1.00 |
| Paraffinic oil | Semtol 70 | 6.40 |
| POE 30 castor oil | Witconol 300 | 18.00 |
| Polysorbate 80 | Tween 80 | 18.00 |
| 1-hexanol | Epal 6 | 54.20 |

The emulsifiable composition was made by blending all ingredients together and stirring until dissolved.

Soluble Granule Formulation of Emamectin Benzoate

| Ingredient | Trade name | % w/w |
| --- | --- | --- |
| Emamectin Benzoate | (Technical AI) | 5.31 |
| Polyorganosiloxane | Rhodorsil EP 6703 | 0.10 |
| Sodium alkyl naphthalene sulfonates | Sellogen DFL | 1.00 |
| Sodium N-methyl N-oleyl taurate | Adinol OT-64 | 7.50 |
| Anhydrous lactose | Direct Tableting Grade | 86.09 |
|  |  | kg |
| Emamectin Benzoate | (Technical AI) | 1.078 |
| Polyorganosiloxane | Rhodorsil EP 6703 | 0.020 |
| Sodium alkyl naphthalene sulfonates | Sellogen DFL | 0.200 |
| Sodium N-methyl N-oleyl taurate | Adinol OT-64 | 1.500 |
| Anhydrous lactose | Direct Tableting Grade | 17.207 |
| Water | (Technical) | 2.795 |

The soluble granule formulation was prepared as follows on a pilot scale in 5×20 kg lots to give 100 kg of formulation. The first step in the process was the dry blending of the active ingredient emamectin benzoate with the excipients followed by the addition of approximately 14% by weight of water in a 60 liter portable blender. The wet mass was then transferred to a basket extruder filled with a 0.8 mm screen. The extrudate was dried on a fluidized bed dryer for approximately 12 minutes at about 60° C. The granules were transfered to sieving equipment where particles outside the specified range of 4 to 50 mesh were segregated. The overall campaign yield was 91% with yield losses due to segregation of product falling outside the particle size specification. The final product meeting the particle size was bulk packaged in 10 kg bags.

Soluble Granule Formulation of Emamectin Benzoate

| Ingredient | Trade name | % w/w |
| --- | --- | --- |
| Emamectin Benzoate | (Technical AI) | 5.20 |
| Polyorganosiloxane | Antifoam/ Rhodorsil EP-6703 | 0.10 |
| Sodium alkyl naphthalene sulfonates | Sellogen DFL | 1.00 |
| Sodium N-methyl N-oleyl taurate | Adinol OT-64 | 7.50 |
| Lactose | Lactose DCL 21 | 86.2 |
|  |  | kg |
| Emamectin Benzoate | (Technical AI) | 5.12 |
| Polyorganosiloxane | Antifoam/ Rhodorsil EP-6703 | 0.098 |
| Sodium alkyl naphthalene sulfonates | Sellogen DFL | 0.984 |
| Sodium N-methyl N-oleyl taurate | Adinol OT-64 | 7.38 |
| Lactose | Lactose DCL 21 | 84.88 |
| Water | (Technical) | 10.0 |

The soluble granule formulation was prepared on a larger scale in 8×100 kg lots to give 800 kg of formulation. The first step in the process was the dry blending of the active ingredient emamectin benzoate with the excipients for 5–10 minutes until uniform in a 200 liter blender followed by the addition of approximately 10 kg of water (10–12.5%) in the blender. The water was added as a single spray and blending was continued for 1 minute after addition. It was determined that in large scale formulation, less water was required (presumably due to the humidity of the lactose, variation in the temperature of the mixer or the difference in batch size). The wet mass was then transferred to a basket extruder and extruded to a to a 0.8 mm screen into a fluid bed dryer. Each batch was separated into two sub-batches and dried in a single drying cycle without the need for additional stirring during the drying cycle. The extrudate was dried on a fluidized bed dryer for approx. 12–20 minutes at about 60° C. inlet temperature, at air flow 1 m$^3$/min. The granules were transfered vacuum to vibrating sieving equipment where particles outside the specified range of 4 to 50 mesh were segregated. The overall yield was about 90% with yield losses due to segregation of product falling outside the particle size specification. The final product meeting the particle size was bulk packaged.

EXAMPLE 2

Soluble Granule Formulation of Emamectin Benzoate

| Ingredient | Trade name | % w/w |
| --- | --- | --- |
| Emamectin Benzoate | (Technical AI) | 5.5 |
| Fumed silica | Cab-O-Sil M5 | 0.75 |
| Sodium N-methyl N-oleyl taurate | Geropon T77 | 0.75 |
| Polyorganosiloxane | EP 6703 | 0.1 |
| Mixture of anionic surfactants | Witcosperse D60 | 3.0 |
| Starch | Sta-RX | 10.0 |
| Anhydrous lactose | Direct Tableting Grade | 79.9 |

The dry blend soluble granule formulation was made by blending all of the powders together. To the dry blend was added 15% water, and the resulting powder was extruded using a LCI Benchtop extruder with 0.8 mm screen to give wet granules which were then dried overnight at 54° C.

In field studies comparing efficacy described below, the efficacy of the soluble granule formulation was statistically equal to that of the emusifiable composition formulation. Both formulations were tested for acute ocular irritation as described below and it was observed that the emusifiable composition was extremely irritating whereas the soluble granule formulation was only mildly irritating.

EXAMPLE 3

Soluble Granule Formulations of Emamectin Benzoate - Variation of Percentage of Active Ingredient

| Ingredient | (% w/w) | | | | | |
|---|---|---|---|---|---|---|
| | A | B | C | D | E | F |
| Emamectin Benzoate | 1 | 2 | 5 | 10 | 25 | 50 |
| Polyorganosiloxane | 0.1 | 0.1 | 0.1 | 0.1 | 0.1 | 0.1 |
| Sodium N-methyl-N-oleyl taurate | 7.5 | 7.5 | 7.5 | 7.5 | 7.5 | 7.5 |
| Sodium alkyl naphthalene sulfonate | 1.0 | 1.0 | 1.0 | 1.0 | 1.0 | 1.0 |
| Anhydrous lactose | 90.4 | 89.4 | 86.4 | 81.4 | 66.4 | 41.4 |

As demonstrated in this example, the amount of active ingredient (emamectin benzoate) need not be limited to 5% and may be greater than 5%. Each of the noted compositions was prepared by blending the dry powders, adding water, and the extruding the resultant powder using an LCI Benchtop extruder with an 0.8 mm screen to give wet granules which were then dried overnight at 54° C. When dispersed in water, the granules gave a clear solution containing emamectin benzoate.

EXAMPLE 4

Soluble Granule Formulations of Emamectin Benzoate - Variation of Filler

| Ingredient | (% w/w) | | |
|---|---|---|---|
| | A | B | C |
| Emamectin Benzoate | 5.4 | 5.4 | 5.4 |
| Polyorganosiloxane | 0.1 | 0.1 | 0.1 |
| Sodium alkyl naphthalene sulfonate | 1.0 | 1.0 | 1.0 |
| Sodium N-methyl-N-oleyltaurate | 7.5 | 7.5 | 7.5 |
| Hydrous lactose | 86.1 | | |
| Confectioner's sugar (sucrose) | | 86.1 | |
| Powdered glucose | | | 86.1 |

As demonstrated by this example, other water-soluble bio-derived fillers may be used in the practice of the present invention. Each of these compositions was prepared by blending the dry powders, adding water, and extruding the resultant powder by using an LCI Benchtop Extruder with an 0.8 mm screen to give wet granules which were then dried overnight at 54° C. When dispersed in water, the granules gave a clear solution containing emamectin benzoate.

EXAMPLE 5

Soluble Granule Formulations of Emamectin Benzoate - Absence of Surfactants

| Ingredient | (% w/w) | | | |
|---|---|---|---|---|
| | A | B | C | D |
| Emamectin Benzoate | 5.4 | 5.4 | 5.4 | 5.4 |
| Anhydrous lactose | 94.6 | | | 93.6 |
| Hydrous lactose | | 94.6 | | |
| Confectioner's sugar (sucrose) | | | 94.6 | |
| Sodium alkyl naphthalene sulfonate | | | | 1.0 |

As demonstrated by this example, the presence of wetting and/or dispersing surfactants is not necessary for the practice of the present invention. Each of these compositions was prepared by blending the dry powders, adding water, and extruding the resultant powder by using an LCI Benchtop Extruder with an 0.8 mm screen to give wet granules which were then dried overnight at 54° C. When dispersed in water, the granules gave a clear solution containing emamectin benzoate.

EXAMPLE 6

Soluble Granule Formulation of Emamectin Benzoate—Efficacy Study

Performance of the 5% soluble granule formulation of emamectin benzoate (prepared as described in Example 1) was compared with that of the 2% emulsifiable concentrate formulation of emamectin benzoate (prepared as described in Example 1) and the commercial standards lambda-cyhalothrin and esfenvalerate, and the Dipel 2x formulation of *Bacillus thuringiensis kurstaki* when applied weekly for control of tomato fruitworm (*Helicoverpa zea*) on tomato. When applied at 0.0075 lb active ingredient (AI) per acre, both formulations of emamectin benzoate were equally effective and were comparable to the commercial chemical and *B. thuringiensis* standards in reducing fruit damage by *Helicoverpa zea*. The overall mean percentage of damaged fruit in the untreated control was 18.5%, whereas that with the emulsifiable concentrate formulation and soluble granule formulation of emamectin benzoate were 2.0% and 0.5%, respectively. Fruit damage in the lambda-cyhalothrin, esfenvalerate and the *B. thuringiensis kurstaki* treatments averaged 1.0%, 0.0% and 1.5%, respectively.

'Roma' tomato transplants were planted in the field on June 10. Each plot was one row (5 ft centers) by 20 feet (=0.0022957 acre). Plots were separated within rows by at least 6 feet of unplanted ground and across rows by 24 feet. A single row of sweet corn ('Silver Queen') was planted mid-way between rows. Weeds are allowed to grow in the ground between the tomato and sweet corn rows, but were kept mowed. Weeds were controlled within tomato rows by a single application of Sencor 75 DF applied as a directed spray at the rate of 0.5 lb a.i./acre on June 20. Foliar applications of Dithane M45 at 1.5 lb a.i./acre were made every 5 days beginning July 1 and continuing through harvest for control of foliar diseases. In addition, calcium nitrate at 4 lb/acre was applied on July 10, 17, 24 and 31 for control of blossom-end rot. All insecticide treatments were applied as foliar sprays on July 23, 30, August 6, and 13. Applications were made using a $CO_2$-powered, backpack sprayer calibrated to deliver 55 gallons of spray per acre at 42 psi. The spray was delivered through 3 hollow cone nozzles (D-3 disk, 25 core) directing spray toward each side of the row (equivalent 6 nozzles per row). Sprays were initiated on July 23 in response to an increase in capture of *Helicoverpa zea* moths in a nearby blacklight trap and the appearance of *H. zea* eggs on the tomato foliage. The experimental treatments were:

1. Emulsifiable concentrate formulation of 2% emamectin benzoate applied at 0.0075 lb active ingredient per acre
2. Soluble granule formulation of 5% emamectin benzoate applied at 0.0075 lb active ingredient per acre
3. Lambda-cyhalothrin (Karate 1E) applied at 0.02 lb active ingredient per acre
4. Esfenvalerate (Asana XL 0.66 EC) applied at 0.036 lb active ingredient per acre
5. *Bacillus thuringiensis kurstaki* (Dipel 2X) applied at 1.0 lb formulation per acre
6. Untreated control The experimental treatments were replicated 4 times in a randomized complete block experimental design. The incidence of fruitworm damage to the fruit was determined in each plot on August 11, when the first fruit reached market maturity, and again on August 16. On each sample date, 25 randomly selected ripe fruit were harvested and examined for insect damage. Insect damaged fruit were classified as unmarketable and cut open to identify the insect responsible for the damage, if it was present. Undamaged fruit were classified as marketable. All insects found in fruits were *H. zea,* and damage to fruit was, in all cases, characteristic of that caused by *H. zea.* Although the experimental protocol called for three evaluations of damage to fruit, a third evaluation was not possible because southern blight began to spread rapidly through the plots between the first and second harvest. The number of dead and dying plants in the plots rose quickly after the second evaluation and made it impossible to obtain meaningful data from a third harvest. The southern blight first appeared on scattered plants in early July, following excessive rainfall throughout June. Little spread of the disease was observed until after the planting was irrigated on August 8. Because most plants in all plots appeared healthy at the time of each harvest and diseased plants were not harvested, there is no reason to suspect that the incidence of southern blight compromised the data generated in this trial.

Tomato fruitworm was the only insect pest to develop damaging populations in this trial, and the damage levels in the untreated control plots were typical for early August in the Coastal Plain of North Carolina. The percentages of total fruit damaged by *H zea* in the untreated check in the August 11 and 16 samples were 17 and 20 percent, respectively. Unfortunately, the trial was not continued into late August when tomato fruitworm populations reach very high levels. On both harvest dates, all treatments had significantly fewer damaged fruits than the untreated check, and there were no significant differences among any of the experimental treatments. Both formulations provided control of tomato fruitworm comparable to the chemical standards lambda-cyhalothrin and esfenvalerate, as well as the biological standard *B. thuringiensis kurstaki* (Dipel 2X).

These results indicate that both the emulsifiable concentrate formulation and soluble granule formulation of emamectin benzoate were equally effective in controlling tomato fruitworm when each applied on a 7 day schedule at a rate of 0.0075 lb active ingredient/acre. Both formulations were as effective as lambdacyhalothrin at 0.02 lb active ingredient/acre, esfenvalerate at 0.036 lb active ingredient/acre, and the Dipel 2X formulation of *B. thuringiensis* kurstaki applied at 1.0 lb formulation/acre on a 7 day schedule.

In subsequent efficacy studies, the emulsifiable concentrate formulation and soluble granule formulation of emamectin benzoate were equally effective in controlling diamondback moth, fall armyworm and cabbage webworm upon aerial application.

EXAMPLE 7

Soluble Granule Formulation of Emamectin Benzoate—Acute Ocular Irritation Study in Rabbits The potential primary ocular irritation of 5% soluble granule (SG) formulation of the agricultural pesticide emamectin benzoate (prepared as described in Example 1) was evaluated in New Zealand albino rabbits. The study was conducted in accordance with Standard Operating Procedures. Six rabbits (3 males and 3 females) were used in the test group of this study. At the experimental start of the study, the animals were approximately 15 weeks old and ranged in weight from 2.85 to 3.05 kg. On Study Day 0, 100 milligrams of the formulation were placed in the conjunctival sac of the left eye (the right eye was untreated and used as a control). All animals were observed daily for 7 days for mortality and clinical signs. Body weights were recorded for all rabbits on Study Day 0 before administration and on Study Day 7. General survey of the eyes, direct pupillary and corneal reflexes of both eyes, and scoring of ocular reactions of the treated eye, according to Draize scoring system (*J. Pharmacol. Exp. Therap.* 82:377–390 (1944)), were done before treatment 15 and 120 minutes, 24, and 48 and 72 hours, 4 to 7 days after treatment in all rabbits. All rabbits were euthanized on Study Day 9 by an overdose of barbiturate and discarded without necropsy. There were no drug-related in body weight gain, neither clinical signs except ocular signs described below.

At 15 minutes, very slight conjunctival redness, slight chemosis (one animal) and very slight to slight discharge were noted in the treated eyes of all rabbits. By 120 minutes, slight conjunctival redness, slight chemosis and slight discharge (all animals) and slight iritis (2 animals out of 6) were observed. By 24 hours, all previous ocular reactions decreased in severity and only very slight conjunctival redness, and slight iritis (one animal) persisted. However, very slight corneal opacity (<1.4 corneal surface) was present in 2 animals. By 48 to 72 hours, all ocular reactions regressed, and only very slight conjunctival redness lasted in one animal. By Day 4 through Day 7 all rabbit eyes were normal. The values of the Draize scores correlated with the clinical signs. The individual total scores were very low and never exceeded 15 (the maximum score achievable by this method being 110). Throughout the study, direct pupillary reflexes and corneal reflexes were normal in all rabbits. Subsequent testing of a 10% and a 25% soluble granule (SG) formulation of emamectin benzoate suggested that the 10% formulation was moderately irritating, but the 25% formulation exhibited severe irritation.

EXAMPLE 8

Emulsifiable Concentrate Formulation of Emamectin Benzoate—Acute Ocular Irritation Study in Rabbits The purpose of this study was to determine the ocular irritation potential of a 2% Emulsifiable Concentrate (EC) formulation of the agricultural pesticide emamectin benzoate when instilled once in the eye of a rabbit.

One male albino rabbit (New Zealand white) approximately 22 weeks of age and weighing 2.76 kg was used in this study. The animal was housed in an individual stainless steel cage in a temperature-controlled room. The diet consisted of Purina Certified High Fiber Rabbit Chow. Drinking water was available at all times. The rabbit was treated with 0.1 ml of emulsifiable concentrate formulation of emamectin benzoate (prepared as described in Example 1) placed in the conjunctival sac of the left eye. Immediately after administration, the eyelids of the treated eye were held together for one second and released. The right eye was used as an untreated control.

The rabbit was observed for 21 days for signs of systemic toxicity and ocular irritation. Ocular examinations were made pretest and approximately 60 minutes after ocular application and daily thereafter, except for weekends (Days 5, 6, 12, 13, 19, 20). These observations were scored by the Draize Method (J. Pharmacol. Exp. Therap. 82:377–390 (1944)). Body weights were taken pretest and on Days 7, 14 and 21. At the end of the observation period, the rabbit was discarded without necropsy. The formulation did not produce any treatment-related systemic effects or changes in body weight. However, the formulation produced slight opacity covering the whole cornea, moderate redness and chemosis, and severe discharge at 60 minutes. The eye worsened at 24 hours with corneal anesthesia and the iris showing some congestion including circumcorneal injection in addition to the previous signs. The eye slowly improved and from Day 18 to the end of the observation period on Day 21, only corneal anesthesia and very slight opacity covering the whole cornea was seen.

In conclusion, the emulsifiable concentrate formulation of emamectin benzoate was extremely irritating to the eye of a rabbit. Because evidence of ocular irritation was still present after 21 days, no additional rabbits were tested for ocular irritation with the emulsifiable concentrate formulation of emamectin benzoate.

EXAMPLE 9

Neat Emamectin Benzoate—Acute Ocular Irritation Study in Rabbits

The purpose of this study was to determine the ocular irritation potential of neat emamectin benzoate when instilled once in the eye of a rabbit.

Three male and three female albino rabbits (New Zealand white) 25 to 26 weeks of age and weighing 3.23 to 3.66 kg was used in this study. The test compound was ground into a fine powder and a volume of 0.1 cc (approximately 28 mg) was placed in the conjunctival sac of the left eye of each rabbit. Immediately after administration, the eyelids of the treated eye were held together for one second to prevent loss of material and released. The right eye was used as an untreated control.

Ocular examinations were made recorded at 1, 24, 48 and 72 hours post-instillation in all rabbits and were scored by the Draize Method (J. Pharmacol. Exp. Therap. 82:377–390 (1944)). Because of severe ocular reactions, three rabbits were euthanized following the 72-hour reading. Scores were recorded for the three remaining rabbits once daily through 14 days post-instillation except on weekends.

The test compound neat emamectin benzoate was found to be severely irritating to the rabbit eye. At one hour the eyes of four rabbits had congestion of the iris. All of the eyes had corneal anesthesia and conjunctival irritation. The latter consisted of moderate redness, slight or moderate chemosis and severe colorless discharge. Subsequently, the severity of the signs generally increased. At 24 hours an additional rabbit had congestion of the iris. Another animal had very slight corneal opacity covering less than ¼ of the corneal surface. No other opacities were seen. In the three rabbits that were euthanized early, chemosis became severe and interfered with reading some of the other signs. Redness, where seen, also became severe and the discharge consisted mostly of white mucoid material. One eye did not react to light (no blink response). The eyes of these three rabbits mostly remained unchanged through 72 hours. In the eyes of the three remaining rabbits at 24 hours, corneal anesthesia was still present, redness was severe, chemosis was never more than moderate and in two of the eyes white mucoid material appeared in the discharge. The eye of the rabbit with no white mucoid discharge appeared normal in 48 hours and for the remainder of the 14-day observation period. Signs in the other two eyes remained generally unchanged at 48 hours, but subsequently diminished. Corneal anesthesia lasted through 72 hours. On Days 8, 9, and 10, one of the eyes had an unusual red spot that appeared to be in the iris. However, localization was difficult due to positioning of the nictitating membrane. The eye appeared normal by Day 13. The remaining rabbit's eye appeared normal on Days 13 and 14 except for some slight white mucoid discharge. Some body weight loss (less than 7%) occurred in the rabbits euthanized early, otherwise body weight gain appeared unaffected by drug administration.

In conclusion, neat emamectin benzoate itself is a severe, irreversible eye irritant.

TABLE I

FIFRA Toxicity Criteria and Categories

| Acute Hazard Study | Category I | Category II | Category III | Category IV |
|---|---|---|---|---|
| Signal Word | "DANGER" | "WARNING" | "CAUTION" | "CAUTION" |
| Rat Oral $LD_{50}$ (mg/kg) | 0–50 | >50–500 | >500–5000 | >5000 |
| Rabbit Dermal $LD_{50}$ (mg/kg) | 0–200 | >200–2,000 | >2,000–20,000 | >20,000 |
| Rat Inhalation $LD_{50}$ (mg/L) | 0–0.2 | >0.2–2 | >2–20 | >20 |
| Rabbit Ocular Irritation | Corrosive, corneal opacity not reversible within 7 days | Corneal opacity reversible within 7 days; irritation persisting for 7 days | No corneal opacity; irritation reversible within 7 days | No irritation |
| Rabbit Dermal Irritation | Corrosive | Severe irritation at 72 hours | Moderate irritation at 72 hours | Mild or slight irritation at 72 hours |

It is noted that rabbit ocular irritation studies are required for assignment of the appropriate level of precautionary labeling statements which must be made on the product label. For purposes of information, Table I lists the types of hazard studies, the appropriate signal words on the product label and the FIFRA categories (see Federal Insecticide, Fungicide, and Rodenticide Act (Labeling Requirements For Pesticides and Devices, Fed. Reg., pp. 37960–37995, Sep. 26, 1984); 40 C.F.R. §156.10).

Under FIFRA Guidelines, the signal word for the precautionary labeling statements on the product label is determined by ant the most severe result of any of the acute hazard studies conducted. A product in the highest category (Category I, "DANGER") presents increased hazards to the user and in certain cases must be regulated by the EPA as a "Restricted Use Pesticide."

Because ocular irritation studies on the emulsifiable concentrate formulation of 2% emamectin benzoate showed evidence of ocular irritation persisting after 21 days, the formulation is considered a severe irritant and is placed in Category I ("DANGER"). Similarly, the active ingredient itself, neat emamectin benzoate, was also a severe irritant in ocular irritation studies. Surprisingly, however, ocular irritation studies on the soluble granule formulation of 5% emamectin benzoate showed that ocular irritation had cleared within 7 days and that this formulation was only a mild irritant. Accordingly, the soluble granule formulation of emamectin benzoate would be placed in Category III ("CAUTION"). Such results are intended to be representative of the intrinsic advantages which may be afforded by the present invention.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective concentrations other than the particular concentrations as set forth herein above may be applicable as a consequence of variations in the application of the formulations of this invention. Likewise, the specific biological responses observed may vary according to and depending upon the particular active compound selected or whether there are present other pharmaceutical carriers, as well as the specific type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A pesticidal composition in the form of a water-soluble granule comprising:

0.1 to 60% by weight of emamectin benzoate;

40 to 99.9% by weight of lactose;

0 to 25% by weight of sodium N-methyl N-oleyl taurate;

0 to 10% by weight of sodium alkyl naphthalene sulfonate; and 0 to 3% by weight of polyorganosiloxane, wherein the sum of the proportions of emamectin benzoate, lactose, sodium N-methyl N-oleyl taurate, sodium alkyl naphthalene sulfonate and polyorganosiloxane is not greater than 100% by weight.

2. The pesticidal composition of claim 1 comprising:

1 to 50% by weight of emamectin benzoate;

40 to 99% by weight of lactose;

0 to 10% by weight of sodium N-methyl N-oleyl taurate;

0 to 2% by weight of sodium alkyl naphthalene sulfonate; and 0 to 1% by weight of polyorganosiloxane, wherein the sum of the proportions of emamectin benzoate, lactose, sodium N-methyl N-oleyl taurate, sodium alkyl naphthalene sulfonate and polyorganosiloxane is not greater than 100% by weight.

3. A pesticidal composition in the form of a water-soluble granule comprising:

about 5% by weight of emamectin benzoate;

about 86% by weight of lactose;

about 7.5% by weight of sodium N-methyl N-oleyl taurate;

about 1% by weight of sodium alkyl naphthalene sulfonate; and about 0.1% by weight of polyorganosiloxane.

4. A pesticidal composition in the form of a water-soluble granule comprising:

0.1 to 60% by weight of emamectin benzoate;

40 to 99.9% by weight of a water-soluble filler wherein the water-soluble filler is selected from the group consisting of: lactose, sucrose and glucose;

0 to 25% by weight of sodium N-methyl N-oleyl taurate;

0 to 10% by weight of sodium alkyl naphthalene sulfonate; and 0 to 3% by weight of polyorganosiloxane, wherein the sum of the proportions of emamectin benzoate, water-soluble filler, sodium N-methyl N-oleyl taurate, sodium alkyl naphthalene sulfonate and polyorganosiloxane is not greater than 100% by weight.

5. The pesticidal composition of claim 4 comprising:

1 to 50% by weight of emamectin benzoate;

40 to 99% by weight of a water-soluble filler wherein the water-soluble filler is selected from the group consisting of: lactose, sucrose and glucose;

0 to 10% by weight of sodium N-methyl N-oleyl taurate;

0 to 2% by weight of sodium alkyl naphthalene sulfonate; and 0 to 1% by weight of polyorganosiloxane, wherein the sum of the proportions of emamectin benzoate, water-soluble filler, sodium N-methyl N-oleyl taurate, sodium alkyl naphthalene sulfonate and polyorganosiloxane is not greater than 100% by weight.

6. A method for the control of agricultural insects which comprises applying to an area infested with such agricultural insects an effective amount of a solution of the pesticidal composition of claim 1 in a solvent comprising water.

7. A method for the prevention or treatment of insect infestations of plants or plant products which comprises applying to the plant or plant product an effective amount of a solution of the pesticidal composition of claim 1 in a solvent comprising water.

8. A method for the control of agricultural insects which comprises applying to an area infested with such agricultural insects an effective amount of a solution of the pesticidal composition of claim 3 in a solvent comprising water.

9. A method for the prevention or treatment of insect infestations of plants or plant products which comprises applying to the plant or plant product an effective amount of a solution of the pesticidal composition of claim 3 in a solvent comprising water.

10. A method for the control of agricultural insects which comprises applying to an area infested with such agricultural insects an effective amount of a solution of the pesticidal composition of claim 4 in a solvent comprising water.

11. A method for the prevention or treatment of insect infestations of plants or plant products which comprises applying to the plant or plant product an effective amount of a solution of the pesticidal composition of claim 4 in a solvent comprising water.

* * * * *